(12) United States Patent
Portnoy

(10) Patent No.: US 10,318,714 B2
(45) Date of Patent: Jun. 11, 2019

(54) INSULIN PEN SMART ADMINISTRATION AND TEACHING DEVICE

(71) Applicant: CERNER INNOVATION, INC., Kansas City, KS (US)

(72) Inventor: Alan Mark Portnoy, Exton, PA (US)

(73) Assignee: Cerner Innovation, Inc., Kansas City, KS (US)

( * ) Notice: Subject to any disclaimer, the term of this patent is extended or adjusted under 35 U.S.C. 154(b) by 156 days.

(21) Appl. No.: 15/340,273

(22) Filed: Nov. 1, 2016

(65) Prior Publication Data

US 2018/0121630 A1     May 3, 2018

(51) Int. Cl.
*G06F 19/00* (2018.01)
*G09B 23/28* (2006.01)
*A61M 5/00* (2006.01)
*G09B 19/00* (2006.01)

(52) U.S. Cl.
CPC ........ *G06F 19/3468* (2013.01); *G06F 19/326* (2013.01); *G09B 23/285* (2013.01); *A61M 5/008* (2013.01); *A61M 2205/60* (2013.01); *A61M 2205/6072* (2013.01); *G09B 19/00* (2013.01)

(58) Field of Classification Search
CPC ........ A61M 5/002; A61M 5/20; A61J 7/0076; G06F 19/3462; G06F 19/3468; G06F 19/323; G06F 19/3418
USPC .................................................. 700/231–244
See application file for complete search history.

(56) References Cited

U.S. PATENT DOCUMENTS

| | | | | |
|---|---|---|---|---|
| 8,945,066 B2* | 2/2015 | Bochenko | ........... | G06F 19/3456 604/189 |
| 9,053,520 B2* | 6/2015 | Vik | ........................ | G06Q 50/22 |
| 9,555,191 B2* | 1/2017 | Edwards | ............. | A61M 5/2033 |
| 2002/0050462 A1* | 5/2002 | Penney | ................. | A61M 5/002 206/363 |
| 2009/0128330 A1* | 5/2009 | Monroe | ................ | A61M 5/002 340/568.1 |
| 2015/0105903 A1* | 4/2015 | Denny | ................ | G06F 19/3462 700/237 |
| 2015/0251839 A1* | 9/2015 | Denny | ................... | B65D 83/02 340/686.6 |
| 2016/0012205 A1 | 1/2016 | Saint et al. | | |

* cited by examiner

*Primary Examiner* — Timothy R Waggoner
(74) *Attorney, Agent, or Firm* — Shook, Hardy & Bacon L.L.P.

(57) ABSTRACT

Methods, computer systems, and computer-storage medium are provided for insulin pen association. A stand-alone insulin pen administration device integrates with BCMA and EHR systems and also operates independently as an insulin administration patient educational tool. The insulin pen administration device contains a library of insulin products, unique identifiers that allow the pen administration device to identify the correct product (e.g., insulin pen), size, and concentration when the insulin pen is scanned and loaded into the pen administration device or administered to the patient. Additionally, approved insulin protocols (i.e. sliding scales) can be entered into the pen administration device to allow for administration of insulin when these protocols are ordered.

20 Claims, 4 Drawing Sheets

INSULIN PEN SMART ADMINISTRATION AND TEACHING DEVICE

BACKGROUND

Administration of insulin via insulin pens has been widely accepted by patients and providers in the ambulatory setting, and in recent years, the inpatient acute care setting as well. Insulin pens offer several advantages over the traditional insulin vial and syringe. A greater degree of comfort at the injection site and ease of use for the patient provide a better experience. Further, a dial on the insulin pen enables dose selection and makes dose accuracy more precise. Also, a cover or shield provides protection of the needles and helps reduce contamination and prevent needle sticks of healthcare personnel. Further, initiation and education on the use of the insulin pen, during the acute care hospital visit, improves the transition to use in the home/ambulatory setting. Numerous studies have demonstrated that the use of insulin pens in the acute care setting is beneficial to both patients and providers.

However, the use of insulin pens in the acute care setting has also created problems that are unique to this care venue and are not necessarily observed in the ambulatory setting. For example, managing blood glucose control in the hospital setting is more fluid and dynamic due to rapidly changing patient conditions. Consequently, frequent dose changes are common and can require multiple insulin products and dosing regimens. Some regimens require different dosing schemas even with the same insulin product. These complexities have resulted in numerous medication errors and patient safety concerns. The use of barcode medication administration (BCMA) applications has reduced the incidence of insulin administration errors. However, current systems still depend on the clinician manually confirming or keying in the dose of insulin administered. There is no direct integration between the insulin pen administration device (pen or syringe) and the BCMA application.

Further, when using BCMA applications, multiple dosing regimens with the same insulin product require multiple labels and barcodes to be placed on a single insulin pen. This results in confusion for the clinician and requires each new pen to be re-labeled with multiple labels.

Insulin pens are designed for single patient use; however, there have been numerous reports of insulin pens being shared between patients in the hospital setting resulting in cross-contamination and infection control concerns. This problem is frequently attributed to poor practices by healthcare providers.

Other solutions available in the ambulatory setting have attempted to add a processor unit to the inulin pen itself. This provides dosing regimen information to the end user. However, these insulin pen administration devices do not address the multiple regimens that are often required in the hospital setting, do not prevent the clinician from administering the same syringe to multiple patients, and do not integrate directly with BCMA and electronic health record (EHR) applications.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-storage media for insulin pen association. A stand-alone insulin pen administration device integrates with BCMA and EHR systems and also operates independently as an insulin administration patient educational tool. The insulin pen administration device contains a library of insulin products, unique identifiers that allow the pen administration device to identify the correct product (e.g., insulin pen), size, and concentration when the insulin pen is scanned and loaded into the pen administration device or administered to the patient. Additionally, approved insulin protocols (i.e. sliding scales) can be entered into the pen administration device to allow for administration of insulin when these protocols are ordered.

BRIEF DESCRIPTION OF THE DRAWINGS

Embodiments are described in detail below with reference to the attached drawing figures, wherein.

DETAILED DESCRIPTION

Figure 1:
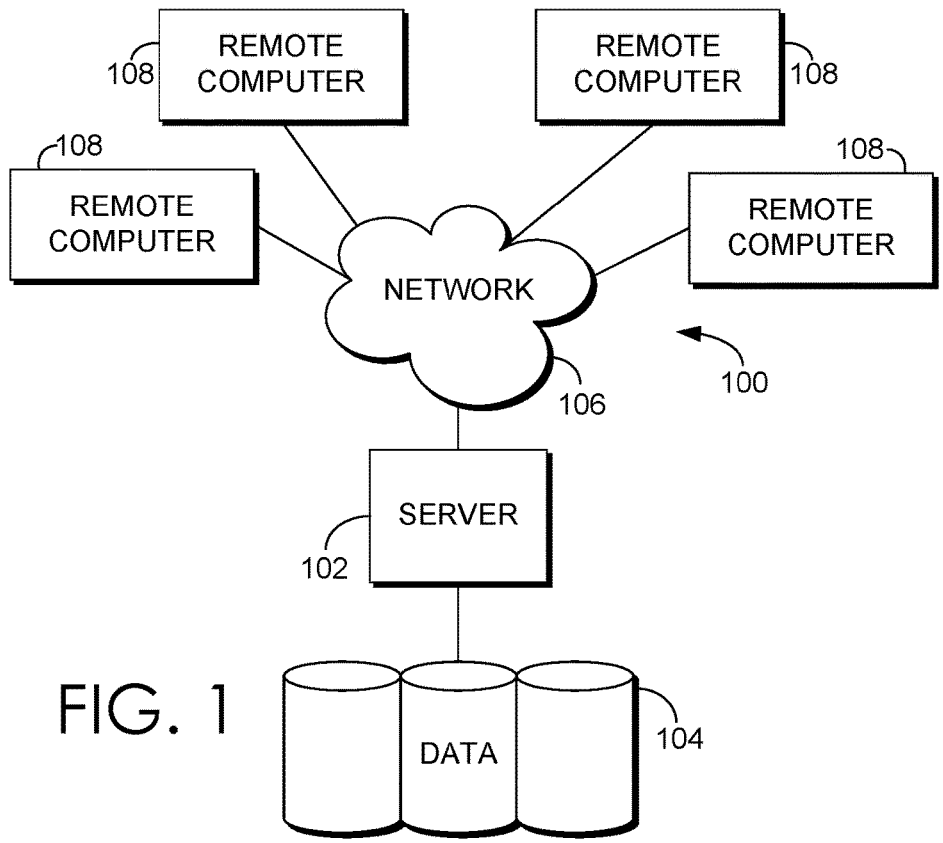
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described. As used herein, the singular forms "a," "an," and "the" are intended to include the plural forms as well, unless the context clearly indicates otherwise.

As noted in the Background, administration of insulin via insulin pens has been widely accepted by patients and providers in the ambulatory setting, and in recent years, the inpatient acute care setting as well. However, the use of insulin pens in the acute care setting has created problems that are unique to this care venue and are not necessarily observed in the ambulatory setting. For example, managing blood glucose control in the hospital setting is more fluid and dynamic due to rapidly changing patient conditions. Consequently, frequent dose changes are common and can require multiple insulin products and dosing regimens. Some regimens require different dosing schemas even with the same insulin product. The use of barcode medication administration (BCMA) applications has reduced the incidence of insulin administration errors. However, current systems still depend on the clinician confirming or keying in the dose of insulin administered and there is no direct integration between the insulin pen administration device (pen or syringe) and the BCMA application.

Further, when using BCMA applications, multiple dosing regimens with the same insulin product require multiple labels and barcodes to be placed on a single insulin pen. This results in confusion for the clinician and requires each new pen to be re-labeled with multiple labels. Insulin pens are designed for single patient use; however, there have been numerous reports of insulin pens being shared between patients in the hospital setting resulting in cross-contamination and infection control concerns. This problem is frequently attributed to poor practices by healthcare providers.

Other solutions available in the ambulatory setting have attempted to add a processor unit to the inulin pen itself. While this provides dosing regimen information to the end user, these insulin pen administration devices do not address the multiple regimens that are often required in the hospital setting, do not prevent the clinician from administering the same syringe to multiple patients, and do not integrate directly with BCMA and electronic health record (EHR) applications.

Embodiments of the present invention are directed to insulin pen association that provides patient safety benefits for the use of insulin pens in the hospital setting. Embodiments can also provide electronic confirmation and documentation of the insulin dose administered to the patient. Additionally, embodiments can provide education to patients on the correct usage of insulin pens in the outpatient setting.

To do so, a stand-alone insulin pen administration device integrates with BCMA and EHR systems and also operates independently as an insulin administration patient educational tool. The insulin pen administration device contains a library of insulin products, unique identifiers that allow the pen administration device to identify the correct product (e.g., insulin pen), size, and concentration when the insulin pen is scanned (with a barcode scanner) and loaded into the pen administration device or administered to the patient. Additionally, approved insulin protocols (i.e. sliding scales) can be entered into the pen administration device to allow for administration of insulin when these protocols are ordered.

The insulin pen administration device securely holds multiple insulin pens in separate channels. Each channel holds one insulin pen that can be scanned to identify the specific insulin product using an internal library of drug products. A controller cap in each channel (attached to the pen administration device by a retractable I/O cable) fits securely to the dosing knob end of each insulin pen. The entire pen administration device is associated with a single patient's EHR utilizing a BCMA server and a unique patient identifier (e.g., medical record number, account number, etc.). This can be accomplished by scanning a unique barcode on the pen administration device after selecting the patient via the BCMA server.

Once the pen administration device has been electronically associated with a patient, separate barcode scans of the individual insulin pens that will be held in the pen administration device, for the patient, can be associated with specific insulin orders also via the BCMA server. The pen administration device communicates wirelessly, via a wireless network, to a server running the pen administration application software. A bi-directional interface to communicate patient and order specific data exists between the pen administration device server and the BCMA and/or EHR server. A display on the pen administration pen admin device provides patient, order, and product confirmation information at various stages of the workflow.

Accordingly, in one aspect, an embodiment of the present invention is directed an insulin pen administration device comprising: a plurality of channels in the insulin pen administration device, each channel having a crossbar and swing arm that locks an insulin pen into each channel preventing unauthorized removal or incorrect insulin pen removal; a barcode scanner integrated into the insulin pen administration device that is used to scan each insulin pen for assignment to a specific channel of the plurality of channels; a controller cap that attaches to a dosing knob end of each insulin pen and attaches to the insulin pen administration device by a retractable I/O cable.

In another aspect of the invention, an embodiment is directed to a computer-implemented method. The method comprises receiving a scanned barcode attached to an insulin pen via a barcode reader attached to a pen administration device. The method also comprises receiving a user interaction at a function button beneath any open channel of the pen administration device. The method further comprises unlocking a crossbar of the pen administration device to enable a user to swing the crossbar to an open position. The method also comprising receiving the insulin pen in the pen administration device. The method further comprises locking the crossbar of the pen administration device to prevent a user from swinging the crossbar to the open position and removing the insulin pen.

In a further aspect, an embodiment is directed to a system in a healthcare computing environment. The system comprises a processor; and a non-transitory computer storage medium storing computer-useable instructions that, when used by the processor, causes the processor to: access a patient, via a barcode medication administration (BCMA) application, to be associated with the insulin pen administration device; select, via the BCMA server, a first insulin order to be administered for the patient causing the BCMA server to enter a pairing mode; scan, via a scanner associated with the BCMA server, a barcode identifier on an insulin pen administration device; communicate insulin order information from the BCMA server to the insulin pen administration device; receive a selection of an insulin product to be administered; guide the clinician to a channel on the insulin pen administration device via a visual indicator; and unlock the crossbar of the pen administration device to allow the clinician to swing the crossbar to the open position and remove an insulin pen contained in the channel.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer storage media does not comprise signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
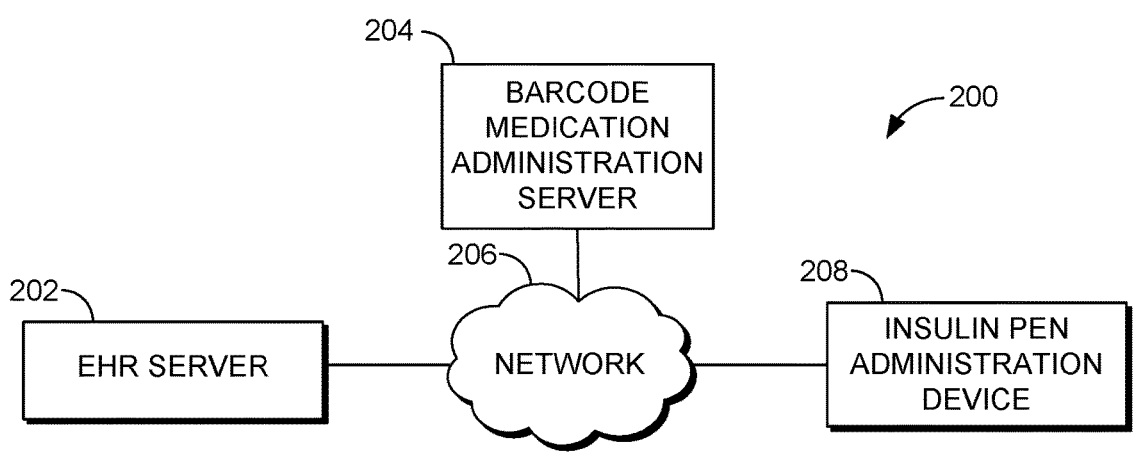
FIG. 2 is a block diagram of an exemplary system suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes an electronic health record (EHR) server 202, a barcode medication administration (BCMA) server 204, and an insulin pen administration device 208, all in communication with one another via a network 206. The network 206 may include, without limitation, one or more secure local area networks (LANs) or wide area networks (WANs). The network 206 may be a secure network associated with a facility such as a healthcare facility. The secure network 206 may require that a user log in and be authenticated in order to send and/or receive information over the network 206.

In some embodiments, one or more of the illustrated components/modules may be implemented as stand-alone applications. In other embodiments, one or more of the illustrated components/modules may be integrated directly into the operating system of the EHR server 202. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the EHR server 202 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The EHR server 202 may store EHRs of patients associated with one or more healthcare facilities. EHRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

The BCMA server 204 may be any type of computing device, such as control server 102 of FIG. 1. BCMA server 204 communicates with a barcode scanner (that may be integrated with the insulin pen administration device 208) that is configured to scan barcodes on various devices (e.g., the insulin pen administration device 208), orders (e.g., medications), and/or patients. The information scanned from the barcodes enables the BCMA server 204 to associate the devices, orders, and/or patients with each other. The BCMA server 204 also communicates information corresponding to the devices, orders, and/or patients and any respective associations to the EHR server 202 where it can be stored in an EMR.

The insulin pen administration device 208, described in more detail below, comprises a plurality (e.g., 2-4) of individual channels that can be loaded with one insulin pen per channel. Each insulin pen may be held in place by rubber calipers that are spring loaded. As can be appreciated, the rubber calibers being spring loaded helps to accommodate insulin pens of various sizes and shapes. The insulin pen administration device 208 may also have an integrated barcode scanner to scan insulin pen products for assignment to a specific channel. A controller cap for each channel enables communication between the insulin pens and the EHR server 202, the BCMA server 204, and/or the insulin pen administration device 208. A multi-function display (MFD) displays patient, product and order information. The information may include communications initiated by and/or received by the EHR server 202, the BCMA server 204, and/or the insulin pen administration device 208. Embodiments are not intended to be limited to visual display but rather may also include audio presentation, combined audio/visual presentation, and the like.

In embodiments, insulin pen administration device 208 can be used in an education mode where the patient's prescribed insulin regimen is programmed into the insulin pen administration device 208. This can assist patients initiated on insulin therapy or those who are new to using an insulin pen in receiving education on proper product selection and use prior to discharge from the hospital. The insulin pen administration device 208 can operate in a teaching mode to quiz the patient by displaying different questions related to their dosing regimen via the display. For example, the patient may be provided with an example blood glucose reading on the display and the insulin pen administration device 208 prompts the patient to perform the appropriate insulin and dose selection. The insulin pen administration device 208 may provide corrective actions if the patient makes an error. Additionally, the insulin pen administration device 208 can confirm that the patient selects the correct product for a particular time of day. While in teaching mode, the channels of the insulin pen administration device 208 may not be locked. The insulin pen administration device 208 can also confirm that the patient selects the correct dose when turning the controller cap.

In embodiments, the insulin pen administration device 208 keeps track of all administrations and quantities of insulin remaining in each pen. When a critical threshold is reached in each pen, a re-stock notification may be electronically sent to a pharmacy system.

Components of the EHR server 202, the BCMA server 204, and the insulin pen administration device 208 may include a processing unit, internal system memory, and a suitable system bus for coupling various system components, including one or more data stores for storing information (e.g., files and metadata associated therewith). The EHR server 202, the BCMA server 204, and the insulin pen administration device 208 typically include, or have access to, a variety of computer-readable media.

The computing system environment 200 is merely exemplary. While the EHR server 202 is illustrated as a single unit, it will be appreciated that the EHR server 202 is scalable. For example, the alert service 216 may in actuality include a plurality of computing devices in communication with one another. Moreover, the data store 220, or portions thereof, may be included within, for instance, the EHR server 214, the alert service 216, and/or the mobile device 218 as a computer-storage medium. The single unit depictions are meant for clarity, not to limit the scope of embodiments in any form.

Figure 3:
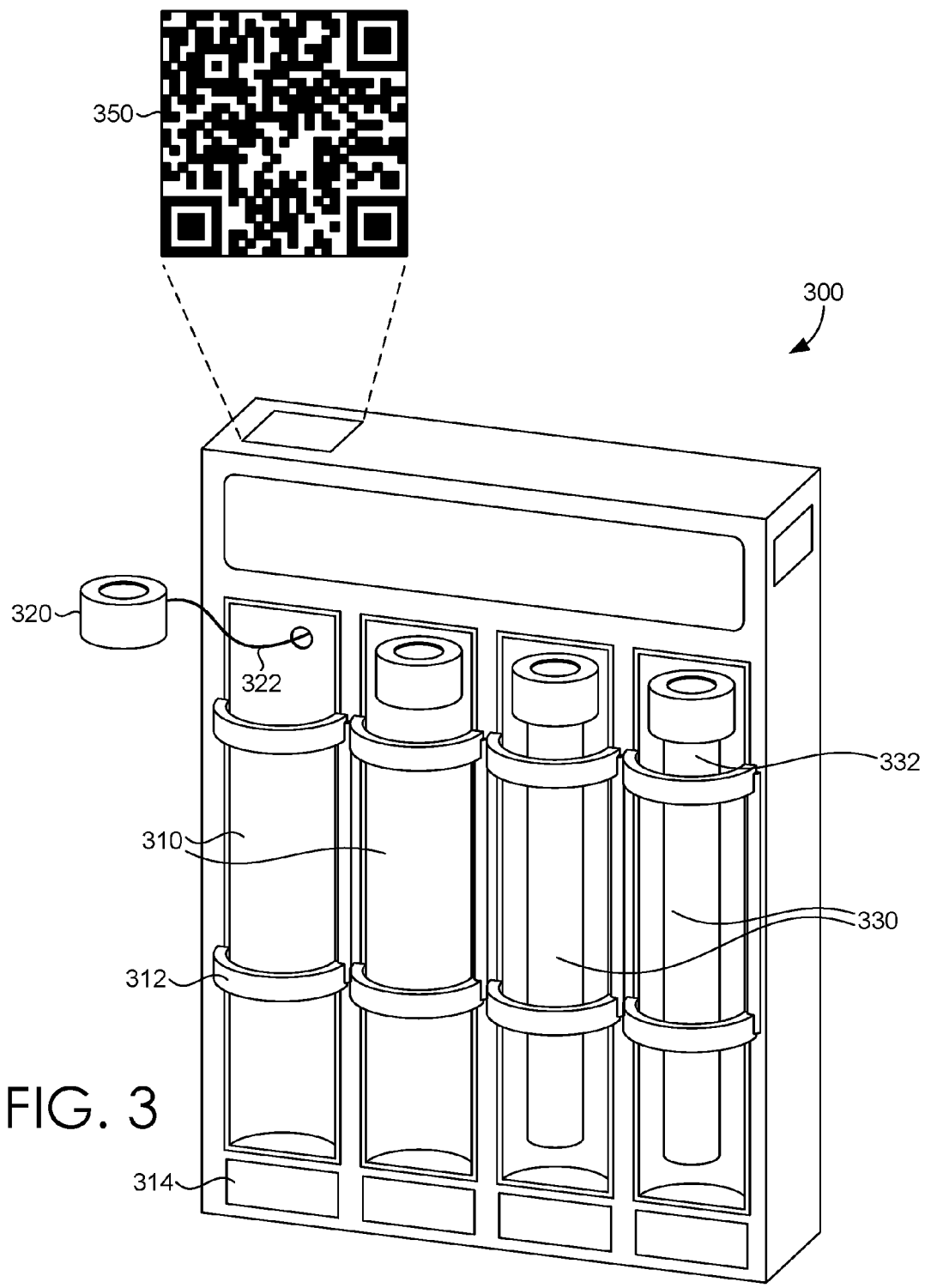
FIG. 3 is a perspective view of an exemplary insulin pen administration device in accordance with an embodiment of the present invention.

Referring next to FIG. 3, an exemplary insulin pen administration device 300 is illustrated. As shown in FIG. 3, the insulin pen administration device 300 comprises a plurality of individual channels 310 that may each be loaded with an insulin pen 330. Spring loaded rubber calipers (not shown in FIG. 3) help secure the loaded insulin pens in each channel 310. Each channel also contains a controller cap 320 that attaches to the dosing knob end 332 of each insulin pen 330. The controller cap may be attached to the insulin pen administration device 300 by a retractable I/O cable 322.

In practice, the controller cap 320 may be calibrated when placed on the dosing knob end 332 of the insulin pen 330. When a new insulin pen 330 is loaded into the insulin pen administration device 300 it is set to zero units. Once the product information identified such as by scanning the medication with the barcode scanner, the insulin pen administration device 300 knows exactly what the insulin dose is selected since the controller cap 320 turns the insulin pen dosing knob. The controller cap 320 can detect each individual "click" when the pen's dosing knob is turned so that exact doing information is communicated back to the insulin pen administration device 300 and the EHR server and/or BCMA server. An audible alert can sound if the user turns the cap passed the prescribed dose for a specific order. Alternatively, a built in servo in the cap can prevent the cap from being turned passed the prescribed dose.

Each channel 310 may also contain a crossbar 312 that locks the insulin pen 330 into each channel. This crossbar 312 prevents removal of the insulin pen 330 from the channel 310. It locks into place and only unlocks when the correct patient and insulin order is selected and scanned using the BCMA server. The crossbar 312 may prevent unauthorized access and/or make certain that the clinician can only remove the correct insulin product (e.g., insulin pen). For example, once an order is selected in the BCMA application (via the BCMA server), the order is communicated to the insulin pen administration device 300. The only crossbar that will unlock is the one that has the correct insulin pen product to fulfill that order. The retractable I/O cable 322 ensures that the clinician returns the insulin pen 330 to the insulin pen administration device 300. Once re-locked, the clinician cannot use that insulin pen 330 on a different patient, which helps prevent cross contamination and infection control issues.

A function button 314 corresponding to each channel serves to acknowledge multiple workflow events and actions. For example, multiple insulins and multiple insulin orders may be associated with one patient using the insulin pen administration device 300. A unique identifier (barcode) 350 is affixed to the insulin pen administration device 300. Using a BCMA server, the barcode 350 is scanned to associate a patient with the insulin pen administration device 300. In embodiments, only one patient can be associated with one insulin pen administration device 300 at any time. A patient must be disassociated from the insulin pen administration device 300, all insulin pens must be removed from the insulin pen administration device 300, and the insulin pen administration device 300 must be cleared prior to associating another patient with the insulin pen administration device 300.

Figure 4:
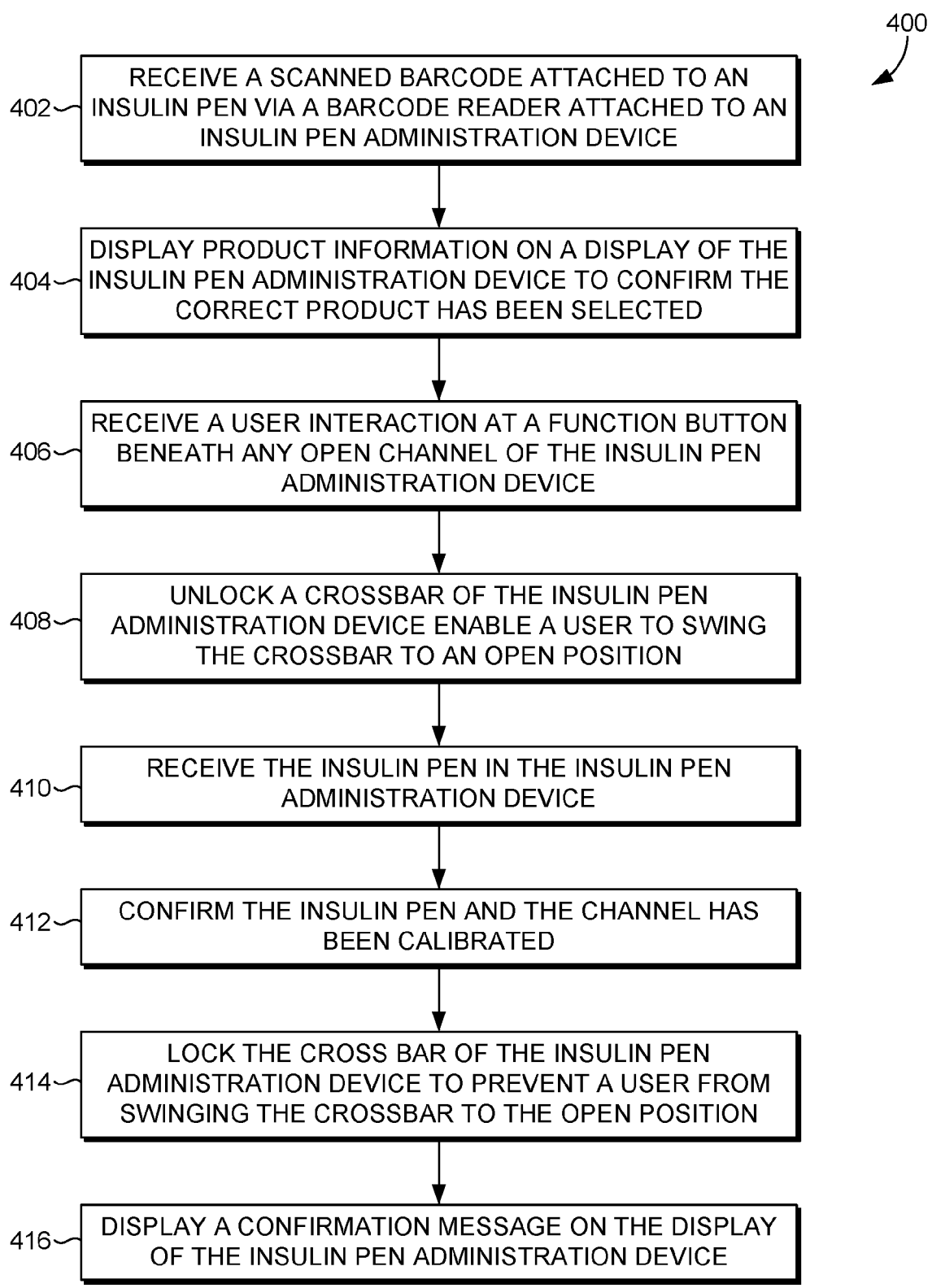
FIGS. 4-6 are flow diagrams of exemplary methods of insulin pen association in accordance with embodiments of the present invention.

In FIG. 4, a flow diagram is depicted of an exemplary method 400 of providing insulin pen association, in accordance with an embodiment of the present disclosure. For instance, the method 400 may be employed utilizing the computing system environment 200 of FIG. 2. As show at step 402, a scanned barcode attached to an insulin pen is initially received via a barcode reader attached to an insulin pen administration device. Product information for the insulin pen may be displayed, at step 404, on a display of the insulin pen administration device. This may help a user (e.g., a clinician) confirm the correct product has been selected.

A user interaction is received, at step 406, at a function button beneath any open channel of the pen administration device. For example, the user may identify which channels in the pen administration device do not currently have an insulin pen. Once an open channel is identified, the user may interact with the function button beneath that open channel.

After the user interaction is received, a crossbar of the insulin pen administration device is unlocked, at step 408. This enables the user to swing the crossbar to an open position and place the insulin pen in the administration device. At step 410, the insulin pen is received in the pen administration device. In some embodiments, as shown at step 412, it is confirmed that the insulin pen and the channel has been calibrated. To calibrate the insulin pen and the channel, prior to closing the crossbar of the insulin pen administration device to secure the insulin pen in place, the controller cap must be attached to the dosing knob on the insulin pen and confirming that the pen is set to zero units.

Upon the user swinging the crossbar into a closed position, the crossbar of the pen administration device is locked, in embodiments, at step 414, to prevent the user (or anyone else) from swinging the crossbar to the open position and removing the insulin pen. A confirmation message may be displayed on the insulin pen administration device, at step 416, confirming the insulin pen is properly loaded and locked in the insulin pen administration device.

Figure 5:
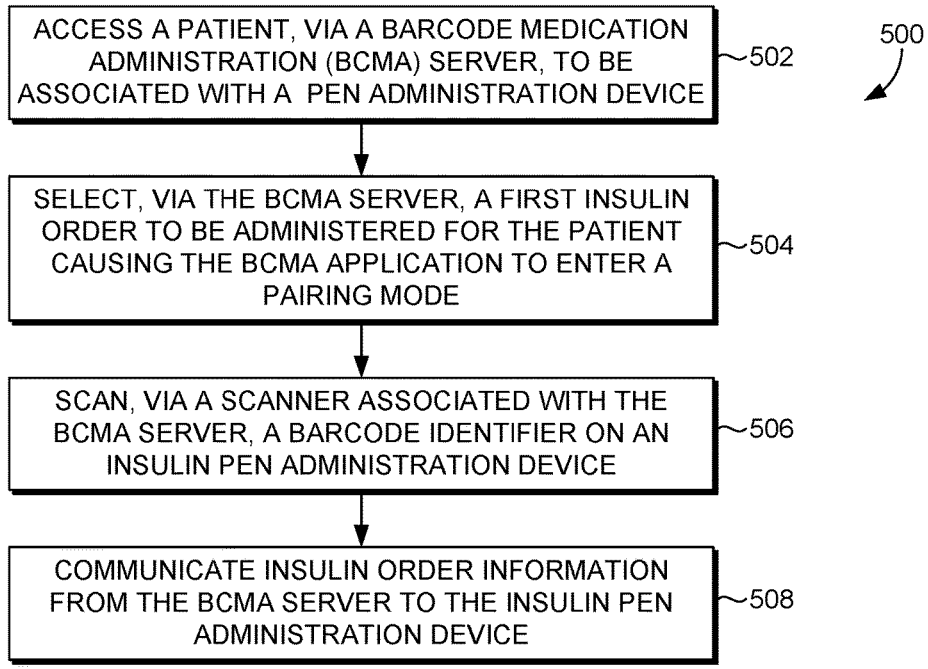

Turning now to FIG. 5, a flow diagram is depicted illustrating an exemplary method 500 of providing insulin pen association, in accordance with an embodiment of the present disclosure. For instance, the method 500 may be employed the computing system environment 200 of FIG. 2. As shown at step 502, a patient is accessed, via a BCMA server, to be associated with the insulin pen administration device. A first insulin order to be administered for the patient may be selected, at step 504, via the BCMA server, causing the BCMA server to enter a pairing mode. A barcode identifier on an insulin pen administration device can then be scanned, at step 506, via a scanner associated with the BCMA server. Insulin order information can then be communicated, at step 508, from the BCMA server to the insulin pen administration device.

In embodiments, an alert may be provided on the display of the insulin pen administration device if the insulin pen administration device has already been associated with a different patient. As mentioned above, only one patient can be associated with one insulin pen administration device at any time. If the insulin pen administration device has already been associated with a different patient and an alert is provided, the user may be prompted to disassociate the device from the different patient and clearing out prior data. Further, removal of any insulin pen products secured in the insulin pen administration device may be required.

In embodiments, an alert may additionally be provided on the display of the insulin pen administration device if the correct insulin product has not been loaded into the device to fulfill the order communicated from the BCMA application (via the BCMA server). In this case, an alert message is provided on the display of the insulin pen administration device alerting the user that the correct product is not loaded in the device.

Figure 6:
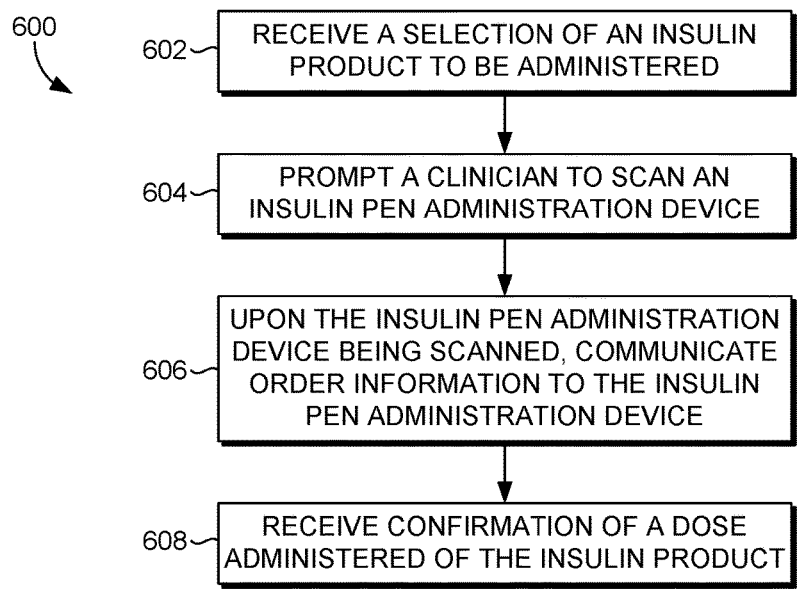

Referring next to FIG. 6, a flow diagram is depicted illustrating an exemplary method 600 of providing closed loop alert management, in accordance with an embodiment of the present disclosure. For instance, the method 600 may be employed the computing system environment 200 of FIG. 2. As show at step 602, a selection of an insulin product to be administered by a clinician is received. The clinician may be prompted, at step 604, to scan an insulin pen administration device. The clinician may additionally be guided to a correct channel on the insulin pen administration device housing the correct insulin pen product via a visual indicator on the insulin pen administration device. Insulin order information is communicated, at step 606, from the BCMA server to the insulin pen administration device.

At this point, in embodiments, the crossbar of the pen administration device is unlocked to allow the clinician to swing the crossbar to the open position and remove the insulin pen. The only crossbar that opens is the one based on order information received from the BCMA server. All other crossbars remain locked. A selection of a prescribed dose may then be received by the clinician turning a controller cap on the insulin pen. Again, visual indicators may assist the clinician in turning the controller cap to select the prescribed dose. An alarm may be provided if the clinician turns the controller cap past the prescribed dose. Confirmation of a dose administered of the insulin product is received by the insulin pen administration device at step 608. The confirmation may be communicated to the BCMA server and/or the electronic health record.

As can be understood, embodiments of the present disclosure provide for an objective approach for providing insulin pen association. The present disclosure has been described in relation to particular embodiments, which are intended in all respects to be illustrative rather than restrictive. Alternative embodiments will become apparent to those of ordinary skill in the art to which the present disclosure pertains without departing from its scope.

From the foregoing, it will be seen that this disclosure is one well adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

What is claimed is:

1. An insulin pen administration device comprising:
  a plurality of channels in the insulin pen administration device, each of the plurality of channels having a crossbar and a swing arm that locks an insulin pen into a channel of the plurality of channels preventing unauthorized removal or incorrect insulin pen removal;
  a barcode scanner integrated into the insulin pen administration device that is used to scan the insulin pen for assignment to a specific channel of the plurality of channels;
  a controller cap that attaches to a dosing knob end of the insulin pen and attaches to the insulin pen administration device by a retractable I/O cable.

2. A computer-implemented method comprising:
  receiving a scanned barcode attached to an insulin pen via a barcode reader attached to a pen administration device;
  receiving a user interaction at a function button beneath an open channel of the pen administration device;
  unlocking a crossbar of the pen administration device to enable a user to swing the crossbar to an open position;
  receiving the insulin pen in the pen administration device; and
  locking the crossbar of the pen administration device to prevent a user from swinging the crossbar to the open position and removing the insulin pen, wherein the insulin pen includes a controller cap that attaches to a dosing knob of the insulin pen and attaches to the pen administration device by a retractable I/O cable.

3. The method of claim 2, further comprising displaying product information on a display of the pen administration device to confirm the correct product has been selected.

4. The method of claim 2, further comprising confirming the insulin pen and the channel has been calibrated.

5. The method of claim 4, further comprising receiving a selection of the insulin pen to be administered.

6. The method of claim 5, further comprising guiding the clinician to a correct channel on the insulin pen administration device via a visual indicator.

7. The method of claim 6, further comprising unlocking the crossbar of the pen administration device to allow the clinician to swing the crossbar to the open position and remove the insulin pen.

8. The method of claim 7, further comprising receiving a selection of a prescribed dose by turning the controller cap on the insulin pen.

9. The method of claim 8, further comprising providing an alarm if the clinician turns the controller cap past the prescribed dose.

10. The method of claim 9, further comprising receiving confirmation of a dose administered of the insulin product and communicating the confirmation to the BCMA server and an electronic health record.

11. The method of claim 2, further comprising accessing a patient, via a barcode medication administration (BCMA) server, to be associated with the insulin pen administration device.

12. The method of claim 11, further comprising providing an alert on the display of the insulin pen administration device if the insulin pen administration device has already been associated with a different patient.

13. The method of claim 12, further comprising prompting the user to disassociate the device from the different patient and clearing out prior data.

14. The method of claim 13, further comprising requiring removal of insulin pen products secured in the insulin pen administration device.

15. The method of claim 11, further comprising selecting, via the BCMA server, a first insulin order to be administered for the patient causing the BCMA server to enter a pairing mode.

16. The method of claim 15, further comprising scanning, via a scanner associated with the BCMA server, a barcode identifier on an insulin pen administration device.

17. The method of claim 16, further comprising communicating insulin order information from the BCMA server to the insulin pen administration device.

18. The method of claim 2, further comprising tracking administrations and quantities of insulin remaining in each insulin pen and, upon a critical threshold being reached, providing a re-stock notification to a pharmacy application.

19. The method of claim 2, wherein the pen administration device is operating in a teaching mode and quizzes the user by displaying different questions related to a dosing regimen via a display on the pen administration device.

20. A system in a healthcare computing environment comprising:
   a processor; and
   a non-transitory computer storage medium storing computer-useable instructions that, when used by the processor, causes the processor to:
   accessing a patient, via a barcode medication administration (BCMA) server, to be associated with the insulin pen administration device;
   selecting, via the BCMA server, a first insulin order to be administered for the patient causing the BCMA server to enter a pairing mode;
   scanning, via a scanner associated with the BCMA server, a barcode identifier on an insulin pen administration device;
   communicating insulin order information from the BCMA server to the insulin pen administration device;
   receiving a selection of an insulin product to be administered;
   guiding the clinician to a channel on the insulin pen administration device via a visual indicator; and
   unlocking the crossbar of the pen administration device to allow the clinician to swing the crossbar to the open position and remove an insulin pen contained in the channel, wherein the insulin pen includes a controller cap that attaches to a dosing knob of the insulin pen and attaches to the pen administration device by a retractable I/O cable.

* * * * *